(12) United States Patent
White, Jr. et al.

(10) Patent No.: US 6,241,974 B1
(45) Date of Patent: *Jun. 5, 2001

(54) DENTIFRICE COMPOSITIONS CONTAINING β-PHASE CALCIUM PYROPHOSPHATE AN ANTICALCULUS AGENT, AND FLUORIDE

(75) Inventors: Donald James White, Jr., Fairfield; Edward Russell Cox, Germantown, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/839,225

(22) Filed: Apr. 22, 1997

(51) Int. Cl.[7] .................. A61K 7/16; A61K 7/18
(52) U.S. Cl. .................. 424/52; 424/49; 424/57
(58) Field of Search .......................... 424/49–58

(56) References Cited

U.S. PATENT DOCUMENTS

| | | | |
|---|---|---|---|
| 2,876,167 | * 3/1959 | Manahan | 167/93 |
| 3,112,247 | 11/1963 | Schweizer | 167/93 |
| 3,678,154 | 7/1972 | Widder et al. | 424/52 |
| 3,737,522 | * 6/1973 | Francis | 424/49 |
| 3,737,533 | 6/1973 | Moon et al. | 424/226 |
| 3,934,002 | * 1/1976 | Haefeld | 424/54 |
| 3,959,458 | 5/1976 | Agricola et al. | 424/52 |
| 4,247,526 | 1/1981 | Jarvis et al. | 423/266 |
| 4,515,772 | * 5/1985 | Parran et al. | 424/57 |
| 4,565,691 | 1/1986 | Jackson | 424/52 |
| 4,590,066 | 5/1986 | Parran, Jr. et al. | 424/52 |
| 4,678,662 | * 7/1987 | Chan | 424/57 |
| 4,721,615 | * 1/1988 | Griffith et al. | 424/57 |
| 4,806,339 | * 2/1989 | Parran et al. | 424/52 |
| 4,822,599 | * 4/1989 | Mitra | 424/52 |
| 4,847,070 | * 7/1989 | Pyrz et al. | 424/52 |
| 4,885,155 | * 12/1989 | Parran et al. | 424/52 |
| 4,913,895 | * 4/1990 | Miyake et al. | 424/57 |
| 4,915,937 | * 4/1990 | Amjad | 424/52 |
| 4,966,777 | * 10/1990 | Saffar et al. | 424/52 |
| 4,999,184 | * 3/1991 | Parran et al. | 424/52 |
| 5,011,830 | * 4/1991 | Leonard et al. | 424/57 |
| 5,015,466 | * 5/1991 | Parran et al. | 424/52 |
| 5,015,467 | * 5/1991 | Smitherman | 424/52 |
| 5,017,363 | * 5/1991 | Suhonen | 424/52 |
| 5,094,843 | * 3/1992 | Mazzanobile et al. | 424/52 |
| 5,094,844 | * 3/1992 | Gaffar et al. | 424/52 |
| 5,096,699 | 3/1992 | Gaffar et al. | 424/49 |
| 5,296,214 | * 3/1994 | Gaffar | 424/49 |
| 5,318,773 | * 6/1994 | Winston et al. | 424/52 |
| 5,338,537 | 8/1994 | White, Jr. et al. | 424/52 |
| 5,376,360 | * 12/1994 | Domke et al. | 424/52 |
| 5,424,059 | * 6/1995 | Prencipe et al. | 424/52 |
| 5,451,401 | * 9/1995 | Zerby et al. | 424/57 |
| 5,456,903 | * 10/1995 | Huetter et al. | 424/57 |
| 5,578,295 | * 11/1996 | Francis et al. | 424/57 |
| 5,599,527 | * 2/1997 | Hsu et al. | 424/52 |
| 5,616,314 | * 4/1997 | Gallupo et al. | 424/49 |
| 5,695,745 | * 12/1997 | Barton et al. | 424/49 |
| 5,730,959 | * 3/1998 | Prencipe et al. | 424/52 |
| 5,939,052 | * 8/1999 | White et al. | 424/52 |

FOREIGN PATENT DOCUMENTS 0 236 290 A1    9/1987  (EP) .................. A61K/7/16

* cited by examiner

Primary Examiner—Shep K. Rose
(74) Attorney, Agent, or Firm—Emelyn deLeon Hilano; Angela Marie Stone

(57) ABSTRACT

Disclosed are dentifrice compositions comprising from about 30% to about 45% of β-phase calcium pyrophosphate, an anticalculus agent, a soluble fluoride ion source capable of providing from about 50 ppm to about 3500 ppm of free fluoride ions, and one or more aqueous carriers. The anticalculus agent may be a polyphosphonate source, a polyphosphate source, or a pyrophosphate source.

6 Claims, No Drawings

DENTIFRICE COMPOSITIONS CONTAINING β-PHASE CALCIUM PYROPHOSPHATE AN ANTICALCULUS AGENT, AND FLUORIDE

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel, and dentine. An organic portion is also present and consists of desquamated epithelial cells, leukocytes, salivary sediment, food debris, and various types of microorganisms.

As the mature calculus develops, it becomes visibly white or yellowish in color unless stained or discolored by some extraneous agent. This is undesirable from an aesthetic standpoint. Mechanical removal of calculus periodically by the dentist is routine dental office procedure. A variety of chemical and biological agents have also been suggested to retard calculus formation or to remove calculus after it is formed. Pyrophosphate salts are chemical agents known to have the ability to retard calculus formation as described, for example, in U.S. Pat. No. 4,999,184, issued Mar. 12, 1991, and U.S. Pat. No. 4,590,066, issued May 20, 1986, both to Parran, Jr. et al., the disclosures of which are incorporated herein by reference in their entirety.

In addition to the pyrophosphate salts, polyphosphates are also know to help retard calculus formation. U.S. Pat. No. 4,627,977, issued Dec. 9, 1986, to Gaffar et al. discloses the use of linear molecularly dehydrated polyphosphate salt in combination with two additional ingredients which inhibit enzymatic hydrolysis of the polyphosphate. U.S. Pat. No. 4,247,526, to Jarvis et al., issued Jan. 27, 1981, discloses the use of a pharmaceutically acceptable condensed phosphate salt in addition to trimagnesium phosphate and dicalcium phosphate dihydrate, a calcium containing abrasive. This patent also discloses a method of stabilizing the dicalcium phosphate dihydrate.

As in Jarvis et al., calcium containing abrasives have been used in toothpaste compositions. However, the calcium ions in these materials will complex with free fluoride ions causing a potential decrease in caries efficacy. Therefore, calcium containing abrasives, such as calcium pyrophosphate, are not preferred abrasives in dentifrice compositions comprising free fluoride ions. Calcium containing abrasive compositions comprising a covalently bonded fluoride source, such as monofluorophosphate, are more stable than compositions comprising an ionic fluoride source.

To help stabilize calcium pyrophosphate, β-phase calcium pyrophosphate is formed by the process described by Schweizer, U.S. Pat. No. 3,112,247, issued Nov. 26, 1963. Although fluoride ions are more stable when combined with the β-phase calcium pyrophosphate than untreated calcium pyrophosphate, the β-phase calcium pyrophosphate is still not preferred, as the fluoride stability can still be significantly improved. For example, see U.S. Pat. No. 5,338,537, to White, Jr. et al., issued Aug. 16, 1994. Typical ionic fluoride stability with β-phase calcium pyrophosphate is approximately 50–60% after several months. Although β-phase calcium pyrophosphate is difficult to stabilize with respect to ionic fluoride, β-phase calcium pyrophosphate remains a preferred abrasive because of its superior cleaning properties versus the more commonly used abrasive, such as silica.

Therefore, there is a need to develop stable dentifrice formulas comprising ionic fluoride and β-phase calcium pyrophosphate. The present inventors have discovered that by adding a selected anticalculus agent to β-phase calcium pyrophosphate, the β-phase calcium pyrophosphate can be greatly inhibited from complexing with fluoride. In addition to the maintenance of fluoride stability and therefore, anticaries efficacy, the antitartar activity is also maintained. Therefore, the dentifrice composition comprising a specific amount of β-phase calcium pyrophosphate provides excellent cleaning and anticaries and anticalculus efficacy.

It is an object of the present invention to provide dentifrice compositions providing maximum fluoride stability and excellent cleaning. It is an object of the present invention to provide a dentifrice composition comprising β-phase calcium pyrophosphate, an anticalculus agent, and fluoride ion source. The anticalculus agent may be a diphosphonate source, a polyphosphate source, a pyrophosphate source, or combination thereof.

These and other objects of the present invention will become readily apparent from the detailed description which follows.

All percentages and ratios used herein are by weight of the dentifrice composition, unless otherwise specified. All measurements are made at 25° C., unless otherwise specified.

SUMMARY OF THE INVENTION

The present invention relates to dentifrice compositions comprising from about 30% to about 45% of β-phase calcium pyrophosphate, an anticalculus agent, a soluble fluoride ion source capable of providing from about 50 ppm to about 3500 ppm of free fluoride ions, and one or more aqueous carriers. The anticalculus agent may be a polyphosphonate source, a polyphosphate source, or a pyrophosphate source.

DETAILED DESCRIPTION OF THE INVENTION

The term "dentifrice composition" as used herein means paste, gel, or liquid formulations unless otherwise specified. The dentifrice composition may be in any desired form, such as deep striped, surface striped, multilayered, having the gel surrounding the paste, or any combination thereof. The dentifrice composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity.

The term "dispenser", as used herein, means any pump, tube, or container suitable for dispensing toothpaste.

The term "aqueous carrier" as used herein means any safe and effective materials for use in the compositions of the present invention. Such materials include additional abrasive polishing materials, peroxide sources, alkali metal bicarbonate salts, thickening materials, humectants, water, surfactants, titanium dioxide, buffering agents, antimicrobial agents, flavor system, sweetening agents, xylitol, coloring agents, and mixtures thereof.

The present compositions comprise essential components, as well as optional components. The essential and optional components of the compositions of the present invention are described in the following paragraphs.

β-Phase Calcium Pyrophosphate

β-phase calcium pyrophosphate is required in the present invention. β-phase calcium pyrophosphate prepared according to the teaching of Schweizer, U.S. Pat. No. 3,112,247, Nov. 26, 1963, may be used. The β-phase calcium pyrophosphate is prepared by heating γ-phase calcium pyrophosphate to 700–900° C. to change about 50% of the γ-phase calcium pyrophosphate to β-phase calcium pyrophosphate and then immediately cooling. The β-phase calcium pyrophosphate is present in an amount of from about 6% to about 70%, preferably from about 30% to about 45%, more preferably from about 35% to about 45%, and most preferably from about 38% to about 43%, by weight of the dentifrice composition.

Anticalculus Agents

The anticalculus agents are agents suitable for reducing the amount of calculus. The anticalculus agents improve the β-phase calcium pyrophosphate stability. Preferred anticalculus agents include polyphosphonate sources, polyphosphate sources, pyrophosphate sources, and mixtures thereof. The anticalculus agents may be present singularly or in combination with additional anticalculus agents.

Polyphosphonate Source

The present invention may include a polyphosphonate as the anticalculus agent. Polyphosphonates, as used herein, include diphosphonates, polydiphosphonates, and polyphosphonates. Use of these materials can be as their acids or water-soluble salts. Also applicable are synthetic polymers based upon phosphonates, including polymers of diphosphonic acids and polyphosphonic acids. Phosphonates are compounds characterized as containing a covalent P—C bond, which links the phosphate group to a molecule. Diphosphonates are characterized as containing a P—C—P bond. Preferred diphosphonates include azacycloalkane diphosphonates. The synthesis of these materials is described in U.S. Pat. No. 3,941,772 issued Mar. 2, 1976, to Ploger et al., incorporated herein by reference in its entirety. The sodium salts of azacycloheptylidne-2,2-diphosphonic acid (AHP) and ethane-1-hydroxy-1,1-diphosphonate (EHDP) are preferred. A further description of polyphosphonates is found in U.S. Pat. No. 5,338,537, issued Aug. 16, 1994, to White, Jr. et al., and U.S. Pat. No. 3,678,154, issued Jul. 18, 1972, to Widder et al., both incorporated herein by reference in their entirety. The polyphosphonate is present in an amount of from about 0.1% to about 12%, preferably from about 0.1% to about 6%, and more preferably from about 0.5% to about 2%, by weight of the composition.

Polyphosphate Source

The present invention may include a polyphosphate source as the anticalculus agent. A polyphosphate is generally understood to consist of two or more phosphate molecules arranged primarily in a linear configuration, although some cyclic derivatives may be present. Although pyrophosphates are a polyphosphate, the polyphosphates desired are those having around three or more phosphate molecules. The pyrophosphates are discussed separately. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). These polyphosphates may be used alone or in an combination thereof.

The phosphate sources are described in more detail in Kirk & Othmer, *Encyclopedia of Chemical Technology*, Fourth Edition, Volume 18, Wiley-Interscience Publishers (1996), incorporated herein by reference in its entirety, including all references incorporated into Kirk & Othmer. The polyphosphate source will typically comprise from about 0.5% to about 20%, preferably from about 4% to about 15%, more preferably from about 6% to about 10%, and most preferably from about 7% to about 9%, by weight of the dentifrice composition.

Pyrophosphate Source

Pyrophosphate sources may be present in the dentifrice composition as the anticalculus agent. The pyrophosphate sources useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate source may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%, by weight of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The amount of pyrophosphate salt useful in making these compositions is any tartar control effective amount, and is generally from about 1.5% to about 15%, preferably from about 2% to about 10%, and most preferably from about 2.5% to about 8%, by weight of the composition.

Compositions may also comprise a mixture of dissolved and undissolved pyrophosphate salts. Any of the above mentioned pyrophosphate salts may be used.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Additional optional agents are synthetic anionic polymers, including polyacrylates and copolymers of maleic anhydride or acid and methyl vinyl ether. The linear polymeric polycarboxylates, including Gantrez, are described in U.S. Pat. No. 4,627,977, to Gaffar et al., issued Dec. 9, 1986, incorporated herein by reference in its entirety, including all references included. Other suitable agents include polyamino propoane sulfonic acid (AMPS), zinc citrate trihydrate, polypeptides (such as polyaspartic and polyglutamic acids), and mixtures thereof.

Fluoride Ion Source

The present invention incorporates a soluble fluoride source, also called an ionic fluoride source, capable of providing free fluoride ions. Preferred soluble fluoride ion sources include sodium fluoride, stannous fluoride, and indium fluoride. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions contain a soluble fluoride ion source capable of providing from about 50 ppm to about 3500 ppm, and preferably from about 500 ppm to about 3000 ppm of free fluoride ions.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 20% to about 94%, preferably from about 25% to about 70%, and more preferably from about 30% to about 45%, by weight of the dentifrice composition.

Additional Abrasive Polishing Materials

An additional abrasive polishing material may also be included in the dentifrice compositions. The additional abrasive polishing material contemplated for use in the compositions of the present invention can be any material which does not excessively abrade dentin. Typical abrasive polishing materials include silicas including gels and precipitates; aluminas; phosphates including orthophosphates and polymetaphosphates and mixtures thereof. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Types of silica dental abrasives are described in more detail in Wason, U.S. Pat. No. 4,340,583, issued Jul. 29, 1982, incorporated herein by reference. Silica abrasives described in U.S. Pat. No. 5,589,160, issued Dec. 31, 1996, and U.S. Pat. No. 5,603,920, issued Feb. 18, 1997, both to Rice, are also herein incorporated by reference. The additional abrasive in the toothpaste compositions described herein may be present at a level of from about 0% to about 70% by weight of the composition.

Peroxide Source

The present invention may include a peroxide source. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The present invention compositions typically contain some thickening material or binders to provide a desirable consistency. Preferred thickening agents are carboxyvinyl polymers, carrageenan, hydroxyethyl cellulose, Veegum, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the dentifrice composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. Polyethylene glycols are preferred humectants. The polyethylene glycol may have a molecular weight of from about 200 to about 7,000,000. The humectant generally comprises from about 0% to 70%, and preferably from about 15% to 55%, by weight of the composition.

Water employed in the preparation of commercially suitable oral compositions should preferably be of low ion content and free of organic impurities. Water will generally comprise from about 5% to about 70%, and preferably from about 10% to about 50%, by weight of the composition herein. The amounts of water include the free water which is added plus that which is introduced with other materials, such as with sorbitol, silica, surfactant solutions, and/or color solutions.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

The present composition may contain a buffering agent. Buffering agents, as used herein, refer to agents that can be used to adjust the pH of the compositions to a range of about pH 6.5 to about pH 10. A composition comprising sodium bicarbonate will have a pH of from about 8.5 to about 9.5. The buffering agents include alkali metal hydroxides, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 1% to about 10%, and more preferably from about 1.5% to about 3%, by weight of the present composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

The present invention may also include xylitol. Xylitol is a sugar alcohol that is used as a sweetener and humectant. Xylitol may provide a therapeutic effect, such as an antibacterial or anticaries effect. The present compositions typically comprise xylitol at a level from about 0.01% to about 25%, preferably from about 3% to about 15%, more preferably from about 5% to about 12%, and most preferably from about 9% to about 11%, by weight of the total composition. Alternatively, if xylitol is used as a sweetener, it may be present at a lower level, such as from about 0.005% to about 5%, by weight of the dentifrice composition.

Sweetening agents can be added to the compositions. These include saccharin, dextrose, sucrose, lactose, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents and water soluble antimicrobials such as quaternary ammonium salts and bis-biquanide salts, among others. Triclosan monophosphate is an additional water soluble antimicrobial agent. Other compounds such as bis[4-(R-amino)-1-pyridinium] alkanes are disclosed in U.S. Pat. No. 4,206,215, issued Jun. 3, 1980, to Bailey, incorporated herein by reference. Stannous salts such as stannous pyrophosphate and stannous gluconate and other antimicrobials such as copper bisglycinate, copper glysinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al., incorporated herein by reference. Specific antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 1.5%, by weight of the dentifrice composition.

The dentifrice compositions may be a paste, gel, or any configuration or combination thereof. The dispenser may be a tube, pump, or any other container suitable for dispensing toothpaste. Dual phase dentifrice composition may alternatively be used. Dual compartment packages suitable for this purpose are described in U.S. Pat. No. 4,528,180, issued Jul. 9, 1985; U.S. Pat. No. 4,687,663, issued Aug. 18, 1987; and 4,849,213, issued Jul. 18, 1989, all to Shaeffer, all incorporated herein in their entirety.

Method of Treatment

The present invention compositions additionally relate to a method for reducing the incidence of calculus on dental enamel. The method of treatment herein comprises contacting the dental enamel surfaces in the mouth with the oral compositions according to the present invention.

EXAMPLES & METHOD OF MANUFACTURING

The following examples further describe and demonstrate embodiments within the scope of the present invention. These examples are given solely for the purpose of illustration and are not to be construed as limitations of the present invention as many variations thereof are possible without departing from the spirit and scope. For example, although specific anticalculus agents are chosen for these examples, other agents listed in the specification are also suitable. Additionally, the amount of the ingredients, particularly calcium pyrophosphate, may be varied according to the amounts stated in the specification.

Example I

| Ingredient | Weight % |
| --- | --- |
| Glycerin | 9.80 |
| Water | 19.76 |
| Veegum | 0.39 |
| Sodium Fluoride | 0.24 |
| Sodium Saccharin | 0.26 |
| Spdium Alkyl Sulfate[a] | 3.92 |
| Flavor System | 0.90 |
| β-phase Calcium Pyrophosphate | 39.00 |
| Carboxymethylcellulose | 1.56 |
| Sorbitol[b] | 14.00 |
| Tetrapotassium Pyrophosphate[c] | 6.02 |
| Sodium Acid Pyrophosphate | 2.10 |
| Tetrasodium Pyrophosphate | 2.05 |

Example II

| Ingredient | Weight % |
| --- | --- |
| Glycerin | 11.80 |
| Water | 21.76 |
| Veegum | 0.39 |
| Sodium Fluoride | 0.24 |
| Sodium Saccharin | 0.26 |
| Sodium Alkyl Sulfate[a] | 3.92 |
| Flavor System | 0.90 |
| β-phase Calcium Pyrophosphate | 35.00 |
| Carboxymethylcellulose | 1.56 |
| Sorbitol[b] | 14.00 |
| Tetrapotassium Pyrophosphate[c] | 6.02 |
| Sodium Acid Pyrophosphate | 2.10 |
| Tetrasodium Pyrophosphate | 2.05 |

Example III

| Ingredient | Weight % |
| --- | --- |
| Glycerin | 7.80 |
| Water | 17.76 |
| Veegum | 0.39 |
| Sodium Fluoride | 0.24 |
| Sodium Saccharin | 0.26 |
| Sodium Alkyl Sulfate[a] | 3.92 |
| Flavor System | 0.90 |
| β-phase Calcium Pyrophosphate | 43.00 |
| Carboxymethylcellulose | 1.56 |
| Sorbitol[b] | 14.00 |
| Tetrapotassium Pyrophosphate[c] | 6.02 |
| Sodium Acid Pyrophosphate | 2.10 |
| Tetrasodium Pyrophosphate | 2.05 |

Example IV

| Ingredient | Weight % |
| --- | --- |
| Glycerin | 11.80 |
| Water | 25.25 |
| Veegum | 0.39 |
| Sodium Fluoride | 0.24 |
| Sodium Saccharin | 0.26 |
| Sodium Alkyl Sulfate[a] | 3.00 |
| Flavor System | 0.90 |
| β-phase Calcium Pyrophosphate | 38.00 |
| Carboxymethylcellulose | 1.56 |
| Sorbitol[b] | 14.00 |
| Sodium Acid Pyrophosphate | 1.10 |
| Tetrasodium Pyrophosphate | 3.50 |

[a]27.9% solution
[b]70% solution
[c]60% solution

The dentifrice composition of Examples I–IV are prepared as follows. Add the water and sorbitol and heat to at least 40° C. Then add the saccharin, tetrapotassium pyrophosphate, and sodium acid pyrophosphate. Premix the β-phase calcium pyrophosphate, carboxymethylcellulose, and Veegum before adding to the mixing vessel. Mix well. Premix the tetrasodium pyrophosphate in the glycerin. Add this premix to the mixing vessel. Next, add the fluoride and mix well. Finally, add the flavor and sodium alkyl sulfate and continue to mix until homogeneous.

Example V

| Ingredient | Weight % |
| --- | --- |
| Glycerin | 9.80 |
| Water | 21.49 |
| Veegum | 0.39 |
| Sodium Fluoride | 0.24 |
| Sodium Saccharin | 0.26 |
| Sodium Alkyl Sulfate[a] | 3.92 |
| Flavor System | 0.90 |
| β-phase Calcium Pyrophosphate | 39.00 |
| Carboxymethylcellulose | 1.56 |
| Sorbitol[b] | 19.00 |
| Sodium Hydroxide[c] | 1.44 |
| Azocycoheptane-2,2-Diphosphonic Acid | 2.00 |

[a]27.9% solution
[b]70% solution
[c]50% solution

The dentifrice composition of Example V is prepared as follows. Mix the water, sorbitol, and sorbitol and heat to at least 40° C. Then add the saccharin and diphosphonate. Next, mix in the sodium hydroxide. Premix the β-phase calcium pyrophosphate, carboxymethylcellulose, and Veegum before adding to the mixing vessel. Mix well. Next, add the fluoride and mix well. Finally, add the flavor and sodium alkyl sulfate and continue to mix until homogeneous.

Example VI

| Ingredient | Weight % |
| --- | --- |
| Glycerin | 9.80 |
| Water | 19.93 |
| Veegum | 0.39 |
| Sodium Fluoride | 0.24 |
| Sodium Saccharin | 0.26 |
| Sodium Alkyl Sulfate[a] | 3.92 |
| Flavor System | 0.90 |
| β-phase Calcium Pyrophosphate | 39.00 |

| Ingredient | Weight % |
|---|---|
| Carboxymethylcellulose | 1.56 |
| Sorbitol[(b)] | 14.00 |
| Glass H Polyphosphate | 10.00 |

[(a)]27.9% solution
[(b)]70% solution

The dentifrice composition of Example VI is prepared as follows. Mix the water, sorbitol, and sorbitol and heat to at least 40° C. Add the saccharin followed by the polyphosphate. Premix the β-phase calcium pyrophosphate, carboxymethylcellulose, and Veegum before adding to the mixing vessel. Mix well. Next, add the fluoride and mix well. Finally, add the flavor and sodium alkyl sulfate and continue to mix until homogeneous.

What is claimed is:

1. A dentifrice composition having improved fluoride stability comprising:
    a. from about 30% to about 45% of β-phase calcium pyrophosphate;
    b. from about 0.1% to about 12% of a polyphosphonate source comprising a salt of 1-azacylcoheptylidene-2,2-diphosphonate;
    c. a soluble fluoride ion source capable of providing from about 500 ppm to about 3500 ppm of free fluoride ions; and
    d. from about 42% to about 70% of one or more aqueous carriers.

2. The dentifrice composition according to claim 1 wherein the polyphosphonate source further comprises a salt of ethane-1-hydroxy-1,1-diphosphonate.

3. The dentifrice composition according to claim 2 wherein the soluble fluoride ion source is sodium fluoride.

4. The dentifrice formulation according to claim 3 further comprising a linear polymeric polycarboxylate and an effective amount of one or more antimicrobial agents selected from the group consisting of zinc salts, triclosan, chlorhexidine, cetyl pyridinium chloride, flavor oils, and mixtures thereof.

5. The dentifrice composition according to claim 4 wherein the β-phase calcium pyrophosphate is in an amount of from about 35% to about 45%.

6. A method for reducing the incidence of calculus and caries on dental enamel comprising contacting the enamel surfaces in the mouth with the dentifrice composition according to claim 1.

* * * * *